(12) United States Patent
Gombert et al.

(10) Patent No.: US 9,925,011 B2
(45) Date of Patent: Mar. 27, 2018

(54) SURGICAL ROBOT SYSTEM

(71) Applicant: GOMTEC GMBH, Seefeld (DE)

(72) Inventors: Bernd Gombert, Wörthsee (DE); Leopold Krausen, München (DE)

(73) Assignee: ABB gomtec GmbH, Wörthsee (DE)

( * ) Notice: Subject to any disclaimer, the term of this patent is extended or adjusted under 35 U.S.C. 154(b) by 108 days.

(21) Appl. No.: 14/907,648

(22) PCT Filed: Jul. 23, 2014

(86) PCT No.: PCT/EP2014/002015
§ 371 (c)(1),
(2) Date: Jan. 26, 2016

(87) PCT Pub. No.: WO2015/010788
PCT Pub. Date: Jan. 29, 2015

(65) Prior Publication Data
US 2016/0157942 A1  Jun. 9, 2016

(30) Foreign Application Priority Data

Jul. 26, 2013 (DE) .......................... 10 2013 012 397

(51) Int. Cl.
*A61B 34/30* (2016.01)
*B25J 9/16* (2006.01)
(Continued)

(52) U.S. Cl.
CPC ............. *A61B 34/30* (2016.02); *B25J 9/1666* (2013.01); *A61B 90/03* (2016.02); *A61B 90/361* (2016.02);
(Continued)

(58) Field of Classification Search
None
See application file for complete search history.

(56) References Cited

U.S. PATENT DOCUMENTS

2006/0149418 A1  7/2006  Anvari
2007/0013336 A1*  1/2007  Nowlin .................. B25J 9/1682
                                                    318/568.21
(Continued)

FOREIGN PATENT DOCUMENTS

DE  102006061178  6/2008
EP      2277441   1/2011

OTHER PUBLICATIONS

International Search Report in PCT Application PCT/EP2014/002015, EPO Nov. 10, 2014.

*Primary Examiner* — Ryan Rink

(57) ABSTRACT

The invention relates to a surgical robot system comprising a robot arm (8) installed on a substructure (1), a first control instance (16) for producing control commands for the robot arm (8) on the basis of user inputs, and a second control instance (18), which receives the control commands from the first control instance (16) and checks the control commands with respect to whether the execution of the control commands by the robot arm (8) requires the robot arm to leave a specified occupied space (21, 22) of the robot arm (8) and releases a control command for execution by the robot arm (8) at most to the extent to which the control command can be executed without the robot arm leaving the specified occupied space (21, 22, 30).

13 Claims, 3 Drawing Sheets

(51) Int. Cl.
*A61B 17/00* (2006.01)
*A61B 90/00* (2016.01)

(52) U.S. Cl.
CPC ............... *A61B 2017/00119* (2013.01); *A61B 2017/00477* (2013.01); *A61B 2090/0808* (2016.02); *G05B 2219/45117* (2013.01)

(56) References Cited

U.S. PATENT DOCUMENTS

| | | | |
|---|---|---|---|
| 2008/0015408 A1* | 1/2008 | Paolitto | A61B 17/00234 600/37 |
| 2008/0247506 A1* | 10/2008 | Maschke | A61B 6/12 378/15 |
| 2009/0163928 A1* | 6/2009 | Schena | A61B 19/2203 606/130 |
| 2009/0271036 A1* | 10/2009 | Kock | B25J 9/1666 700/245 |
| 2010/0069920 A1 | 3/2010 | Naylor | |
| 2010/0286712 A1 | 11/2010 | Won | |
| 2013/0085510 A1* | 4/2013 | Stefanchik | G06F 19/3481 606/130 |
| 2016/0113720 A1* | 4/2016 | Lavallee | A61B 17/15 606/130 |

\* cited by examiner

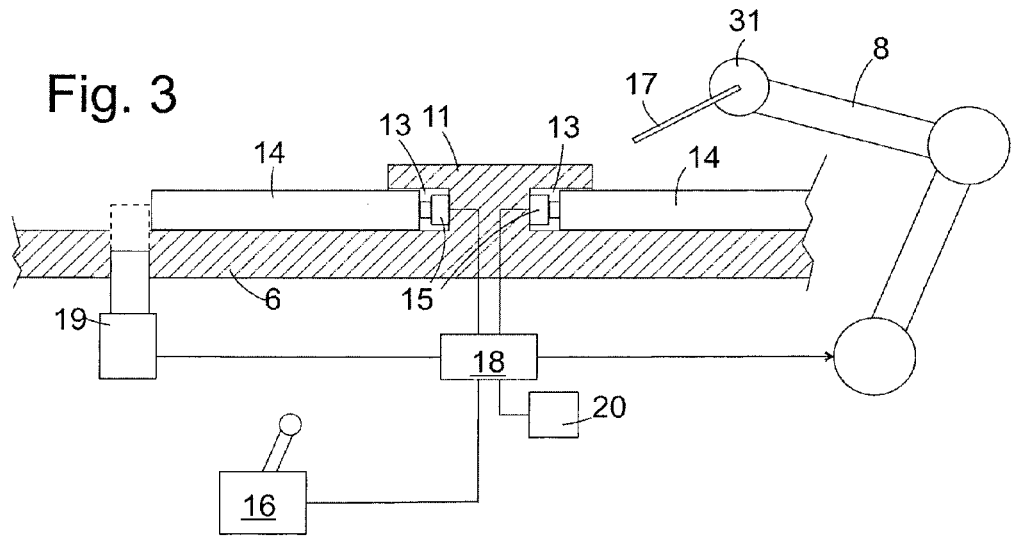
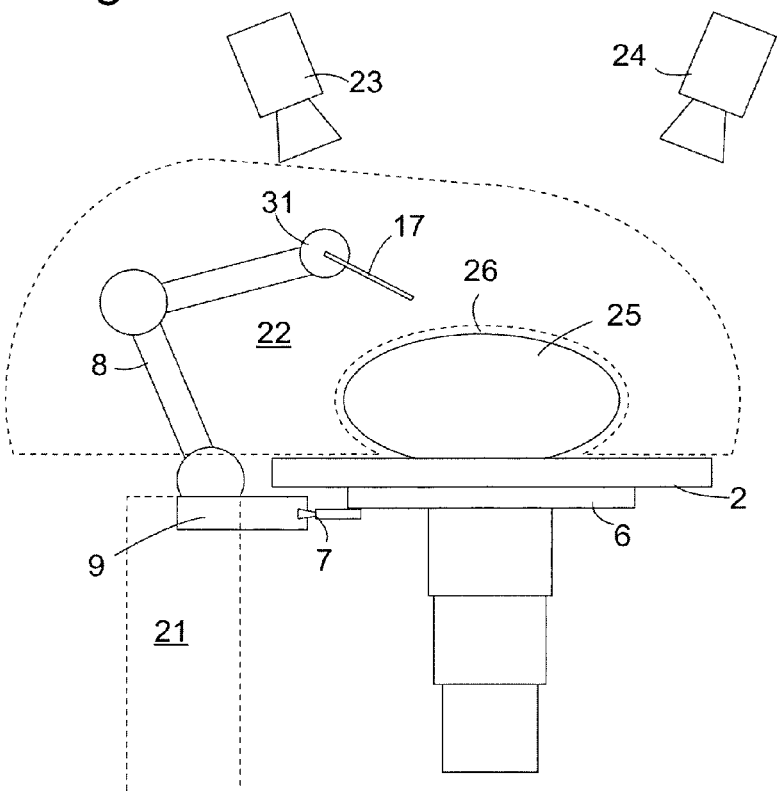

SURGICAL ROBOT SYSTEM

TECHNICAL FIELD

The present invention relates to a surgical robot system for surgical, in particular minimally-invasive, applications. Robots have been widely used in industrial production for many years and make it possible to rationalize production thanks to their ability to reproduce pre-programmed working sequence very quickly and as often as required.

BACKGROUND INFORMATION

Only relatively recently have robotic applications also become of public interest in the field of surgery. In the case of surgical robots, the objective is not the exact repetition of programmed working sequences, since the movements which need to be performed are not repeated from one operation to the next. Unlike industrial robots, surgical robots are not therefore controlled by a fixed program; their movements are defined in each individual case by a surgeon controlling the robot who, whether with the naked eye or with the aid of a camera, observes the robot and its surgical field. In order to operate the robot, the surgeon is preferably provided with a computer-supported control device which is connected with the robot and the camera. In particular, applications in which the surgeon monitors the surgical field by means of a camera are of considerable technical and medical interest. On the one hand, they make it possible for experienced specialists to perform operations without needing to be present in the operating theatre themselves, and thus to treat patients in far distant locations without needing to travel. On the other hand, the camera is an effective means for the surgeon (who may also be present in the theatre) to obtain a view of the inside of the body during the course of a minimally invasive procedure. However, one problem with such operations is that, although the operating surgeon can observe the immediate surgical field by means of the camera and control a surgical instrument held by the robot, information on the wider operating environment, on movements of the auxiliary theatre staff who are present etc. is not accessible through direct sensory impressions. Rather, the operating surgeon's attention is focused on the monitor of the control device which displays the image transmitted by the camera and displays the contents of the control program. However, if the operating surgeon is not precisely aware of the shape of the robotic arm guiding the tool and its possible movements, in extreme cases this can lead to undesired contacts between the robotic arm and the patient's body and can in extreme cases lead to injuries.

Another possible application for robot systems in the operating theatre is to assist a surgeon who is personally present, for example by holding in place tissue parts or body parts of the patient. In the case of orthopedic operations in particular, such assisting activities frequently require the exertion of considerable force, which can exceed the capacities of human assistants but which, in contrast, a robot can apply for an indefinite period without tiring or diminishing in its precision. Advances in automatic speech recognition make it possible for such a robot to respond to spoken instructions by the operating surgeon in a similarly reliable way to human assistants. However, here too it must be ensured that an inappropriate movement on the part of the robot cannot injure the patient. A collision with the robotic arm and the possibility of a resulting injury to the patient should also be reliably ruled out before and after the operation, when transporting a patient to and from the operating and/or preparation room.

The prior are discloses a surgical robot system that comprises a multiple-axis articulated arm robot which carries an x-ray device and a collision-monitoring unit which warns of an impending collision between components of the x-ray device and a patient support arrangement or a patient laid thereon and/or prevents a collision.

SUMMARY

One object of the present invention is to create a surgical robot system with which the danger of undesired contacts between the robotic arm or an instrument guided by the robotic arm and the patient can be minimized.

The problem is solved in that, in the case of a surgical robot system with a robotic arm mounted on a base element, a first control instance for generating control commands for the robotic arm on the basis of user inputs and a second control instance which receives the control commands from the first control instance and checks the control commands with respect to whether the execution of said control commands by the robotic arm requires said robotic arm to leave a specified movement space of the robotic arm, and releases a control command for execution by the robotic arm at most to the extent to which the control command can be executed without the robotic arm leaving the specified movement space, a patient support is detachably connected with the base element and the second control instance is connected with a sensor for detecting whether the base element is connected with the patient support and is configured to base the checking procedure on different movement spaces depending on whether or not the patient support is connected with the base element.

The patient support which is detachably connected with the substructure makes it possible to transport the patient into the theatre on the support, perform the operation while the patient support is connected with the substructure, and then transport the patient out of the theatre again together with the support.

In that the aforementioned checking of the control commands is based on different movement spaces depending on whether or not the patient support is connected with the substructure, the movement space specified when the patient support is not connected can for example define a park position of the robotic arm. The park position can be so selected that in this position the robotic arm is protected from damage and/or does not, as far as possible, impede the connection of the patient support with the substructure. Such a park position can for example be provided adjacent to the substructure, beneath an adapter for the patient support, so that the support, unimpeded by the robotic arm, can be placed on the adapter from any direction. If the patient support is connected with the substructure, the permissible movement space should lie above the patient support so that the robotic arm can perform the necessary work on patients.

The aforementioned limitation of the execution of the control commands can in particular consist in that if the current location of the robotic arm lies within the specified movement space, but the target location of a control command lies outside of this, the path of the robotic arm from the current location to the target location is calculated, a point on this path is determined at which the robotic arm reaches the boundary of the movement space, and the second control instance passes on a modified control command to the robotic arm, the target location of which is this point, so that the movement of the robotic arm ends on reaching the boundary.

In particular, if the movement of the robotic arm consists of numerous small successive individual steps, for example if the movement is controlled by means of a joystick and the position of the joystick unambiguously specifies the target location of the movement, a control command which would take the robotic arm beyond the boundary of the movement space can also be completely suppressed by the second control instance.

The first control instance can for example be a remote user interface which makes it possible for an operating surgeon, who may under certain circumstances not be present in the operating theatre, to guide an instrument held by the robotic arm. This first control instance can also be a speech recognition system which responds to instructions spoken in the operating theatre and translates these into control commands for the robotic arm. In each case the second control instance only allows those commands to be executed as a result of which the robotic arm is not taken out of the specified movement space. If this movement space is suitably defined, any contact between the robotic arm and the patient's body can be prevented.

In an advantageous embodiment of the invention, the movement of the robotic arm or of the instrument guided by the robotic arm is, on gradually approaching the boundary of the movement space, continuously braked until it comes to a standstill, so that an abrupt halting of the movement of the robot and/or instrument on reaching the boundary of the movement space can be avoided.

In order to secure the patient support on the substructure, a locking mechanism can be provided which is movable between a position in which it secures the patient support on the substructure and a position in which it releases the patient support. The locking mechanism can act in a frictionally-locking or in a form-locking manner. The locking mechanism can be operated manually or with the foot. In particular, a bolt can be provided as a locking mechanism which, in the position securing the patient support on the substructure, locks this onto the substructure in a form-locking manner. The aforementioned sensor can be configured to detect the position of this locking mechanism and define the movement space of the robotic arm on the basis of the results of this detection. In this way, a transition of the robotic arm into a movement space suitable for performance of the operation can be prevented until the patient support is attached and secured to the substructure, and the operation cannot begin before the support is properly secured. Conversely, the second control instance can switch back to the park position as movement space as soon as the sensor registers a release of the locking mechanism. In this way an automatic movement into the park position can be ensured if an attempt is made to detach the patient support while the robotic arm is not yet located in the park position.

Alternatively, the locking mechanism can remain locked in the securing position through the second control instance as long as the second control instance bases the checking on the movement space assigned to the patient support being connected with the substructure. In other words, the locking mechanism cannot be opened and the patient support cannot be detached from the substructure as long as the robotic arm is in a movement space suitable for performing an operation. In this case, the park position must be selected as the movement space and moved to by other means before the securing of the locking mechanism is released and the patient support can be removed.

In order to be able, if necessary, to specify a movement space at random or select from several predefined movement spaces, the second control instance can be assigned a user interface.

Preferably, a camera is also connected to the second control instance.

Such a camera can configured to scan a patient on the patient support; the second control instance can then define the movement space of the robot on the basis of the position and the body dimensions of the patient. In order to rule out a contact of the robotic arm with the patient, the patient's body, possibly including a safety zone surrounding them, can be excluded from the movement space which is to be specified. The fact that the robotic arm is prevented in this way from coming into contact with the patient's body does not prevent work from being carried out, since a tool held by the robotic arm for this purpose can project from the movement space of the robotic arm.

The second control instance can also possess an interface for data relating to the operation to be performed on the patient and can be configured to specify the movement space on the basis of this data. If, for example, this data specifies a body part which is to be operated on, the movement space can be specified such that a tool guided by the robotic arm can only reach the body part which is to be operated on. In this way the danger can be reduced that body parts which are not intended to be operated on are accidentally injured or, for example due to a misidentification of the patient, the wrong operation carried out. The interface can for example communicate with the IT system of a hospital in which the robot system according to the invention is being used, but it can also be a wireless interface designed for example to communicate with an RFID element worn by the patient.

It can also be practical for the second control instance to be configured to check whether the specified movement space is accessible for the robotic arm, and to generate an error message if at least a part of the movement space is not accessible and it is therefore not guaranteed that the robotic arm can perform all the movements which might possibly be demanded of it during the course of the operation.

Such a check is in particular advantageous if the robotic arm can be mounted on the base element in different positions.

In order to allow the mounting position of the robotic arm to be taken into consideration when checking the accessibility of the movement space, the second control instance should be configured to detect the position of the robotic arm on the base element.

A surgical tool can be seen as being part of the robotic arm. The tool can comprise a controlled and movable component, for example a gripper.

In order to make possible a controlled advance of such a tool into the body of a patient, the movement space can comprise a surgical field in the body of a patient.

A part of the movement space located outside of the body and the surgical field are preferably connected together via a port.

In an advantageous embodiment of the invention, the base element possesses an electrical energy source for the robot and/or the control instances. The energy source can, depending on its design, be used as a primary power supply unit or as an emergency power supply unit. For example, the energy source can be in the form of a mains power supply, an energy storage device (for example a battery) or a generator. The electrical energy source can thus cover the power supply requirement for the equipment connected thereto, both in normal operation and in emergency operation, for example in the event of a failure of the mains power supply.

BRIEF DESCRIPTION OF THE DRAWINGS

These and other features and advantages of the present invention will be better understood by reading the following detailed description, taken together with the drawings wherein:

FIG. 3 shows a diagrammatic sectional view illustrating the anchoring of the patient support on the base;

FIG. 4 shows a diagrammatic representation of movement spaces of the robotic arm with a patient present on the support;

DETAILED DESCRIPTION OF THE PREFERRED EMBODIMENTS

Figure 1:
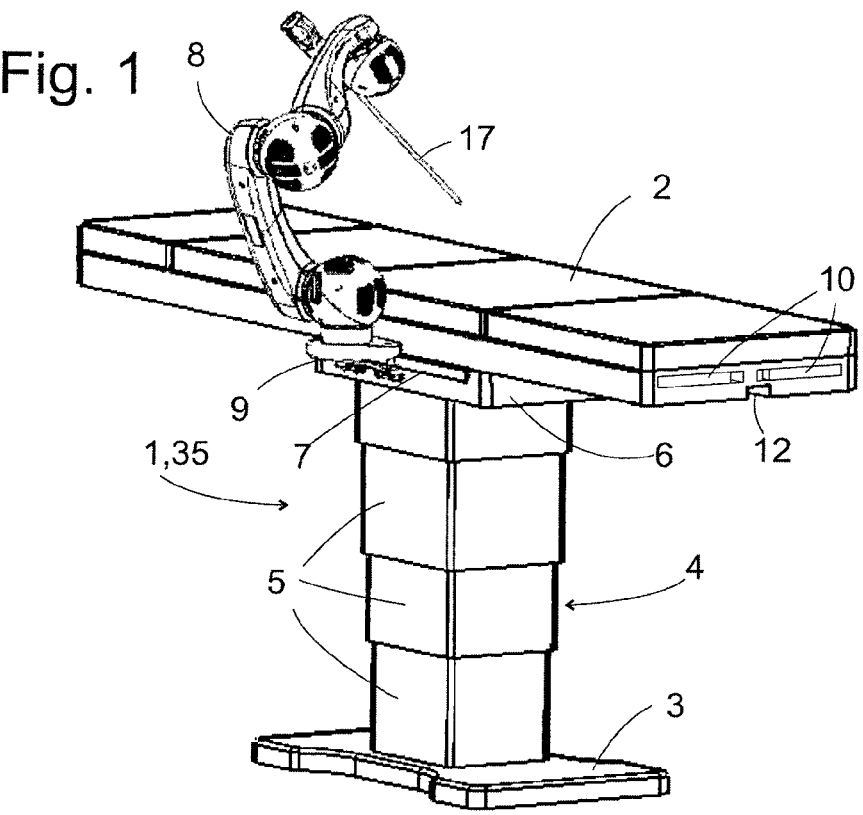
FIG. 1 shows a perspective view of a surgical robot system according to the invention with a patient support and a robotic arm which are mounted on a common base.

FIG. 1 shows the robot system according to a first embodiment of the invention in a perspective view. A base element 1, in this case designed as a pedestal base 35, and a patient support 2 mounted detachably on the base 35 form an operating table. In this case the base 35 comprises a base plate 3 mounted firmly on, for example bolted to, the floor, and a column 4 which in this case is composed of a plurality of telescopically interlocking, height-adjustable segments 5. The upper end of the base 35 is formed by a support plate 6 which supports the patient support 2 and which carries on its longitudinal edge a rail 7, to which a robotic arm 8 is detachably attached. In this case a foot section 9 of the robotic arm 8 comprises two clamping jaws which can be moved relative to one another and which can be clamped onto the rail 7 with the aid of quick-release levers. The quick-release levers make it possible for the robotic arm 8 to be attached to and removed from the base 35 quickly and placed in different positions on the rail 7. In this way, the placement of the robotic arm 8 can be conveniently adapted to the position of a patient on the patient support 2 and the position of a body part which is to be operated on.

The patient support 2 is provided at the head and foot ends with in each case two handles 10 in order to facilitate its handling, if necessary with a patient lying thereon, and its attachment to or removal from the base 35. The handles 10 can be movable between a use position and a sunk-in position in which they do not impede movements of the surgical team around the patient support 2. In this case, the handles 10 can in each case can be swiveled around vertical axes adjacent to the corners of the patient support 2 and in their sunk-in position are accommodated in recesses at the head and foot ends of the patient support 2.

An electronic control unit for controlling movements of the robotic arm 8 can be provided in the base 35, in the robotic arm 8 or also separately from both. The way this control unit functions will be explained later.

According to a variant which is not shown, the base element can also be divided into a first base for the patient support 2 and a second base for the robotic arm, whereby the second base can also be mounted on a wall or a ceiling of the operating theatre.

Figure 2:
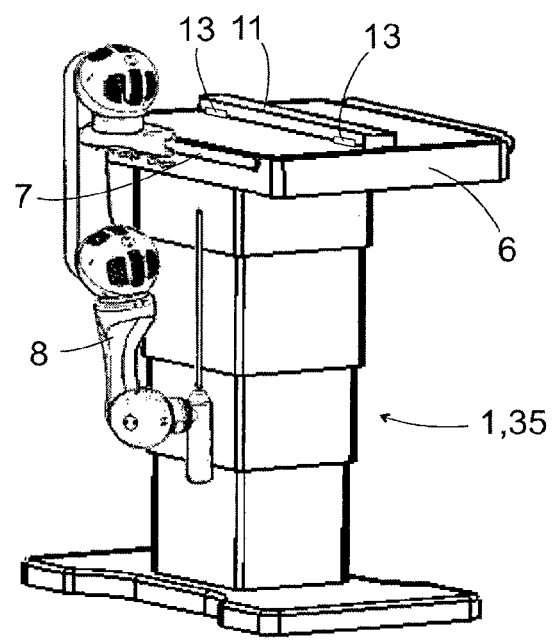
FIG. 2 shows the surgical robot system of FIG. 1 in a configuration in which the patient support has been removed and the robotic arm has been moved into a park position.

FIG. 2 shows the robot system from FIG. 1 in a configuration with the patient support 2 removed. On the now exposed upper side of the support plate 6, a rib 11 extending parallel to the rail 7 is formed which, when the patient support 2 is mounted, engages in a form-locking manner in a groove 12 on its underside (see FIG. 1). In the configuration shown in FIG. 1, the patient support 2 is centrally supported by the base 35; however, it is also conceivable for the patient support 2 to be designed to be slid along the rib 11, allowing the patient support 2 to be fixed on the base 35 in different positions displaced in the longitudinal direction of the rib 11.

According to the embodiment shown in FIG. 2, the rib 11 is provided on its lateral flanks with recesses 13 which, as will be explained in more precise detail in the following, serve to fix the patient support 2 in position.

FIG. 3 shows a diagrammatic cross-section through the rib 11 and its surrounding area at the height of two such recesses 13 arranged opposite one another. Two bolts 14 of the patient support 2 are shown in a position in which they engage in the recesses 13; they are coupled to the handles 10 such that they only engage in the recesses 13 when the handles 10 are in their sunk-in position. In this way it is ensured that, if the handles 10 can be moved into their sunk-in position, the patient support 2 is securely connected with the base 35. A sensor 15, in this case in the form of a mechanical switch, is arranged on the recesses 13 in order to detect the engagement of the bolt 14 and report this to the control unit.

The control unit is divided into a first instance or execution instance 16, the function of which is to receive inputs by an operating surgeon and translate these into control commands which can be executed by the robotic arm 8, and a second or safety instance 18.

According to a first embodiment, the execution instance 16 can comprise a joystick or similar input instrument which can be physically manipulated by the surgeon and which can be moved in several degrees of freedom. Also, a processor can be provided which continuously monitors the movement of the input instrument and at short intervals translates each adjustment of the input instrument into a control command for a movement of the robotic arm 8 proportionate to the detected adjustment.

According to a second embodiment, the execution instance 16 also comprises an input instrument which can be moved in several degrees of freedom and a processor; however, the functional principle of the processor is different: when the input instrument is in an idle position, the processor does not generate any control commands; if the input instrument is deflected from the idle position, it generates control commands in order to move the robotic arm 8 in a direction specified through the direction of the deflection with a speed proportionate to the extent of the deflection.

According to a third embodiment, the execution instance 16 comprises a microphone and a computer-supported speech recognition system which allows it to respond to spoken instructions by a surgeon and so gives the latter the possibility of controlling the robotic arm 4 while simultaneously using his hands to work on the patient himself.

In particular if—as in the case of the first and second embodiment—it can be manually controlled, the execution instance 16 can be positioned physically separate from the other parts of the surgical robot systems. This makes it possible for the surgeon to carry out the operation at a distance from the patient. Even a surgeon who is not physically present in the operating theatre is thus given the possibility of working on the patient with the aid of the robotic arm 8. A camera which supplies this surgeon with the necessary feedback regarding the current position of an instrument 17 held by the robotic arm 8 can be firmly mounted in the operating theatre, for example on its ceiling, above the robot system, or on the robotic arm 8 itself. It can also be an integral part of the instrument 17 held by the robotic arm, for example an endoscope.

The commands from the execution instance 16 are received by a second or safety instance 18 which is also connected with the sensors 15. Depending on the signals from the sensors 15, the safety instance 18 defines a permissible movement space for the robotic arm 8. As long as not all of the sensors 15 register the engagement of a bolt 14 in the corresponding recess 13, and the patient support 2 is, consequently, not securely anchored on the base 1, the permissible movement space of the robotic arm 8 is a park position, which as shown in FIG. 2 extends downwards from the rail 7. In this position, the robotic arm 8 is, on the one hand, protected against impacts, and on the other hand it does not impede the attachment of the patient support 2 to the base 1.

Commands from the execution instance 16 are checked by the safety instance 18 to determine whether their execution would move the robotic arm 8 out of the permissible movement space. If, as in the case of the first embodiment, the commands specify a target location for the movement of the robotic arm 8, it is sufficient to check whether the target location lies outside of the permissible movement space, and not to pass on to the robotic arm 8 a control command in which this is the case. Since a movement of the input instrument is translated into numerous consecutive control commands, the robotic arm 8 can in this way be moved right up to the boundary of the permissible movement space.

If, as in the case of the second embodiment, the commands from the execution instance 16 specify a direction of movement of the robotic arm 8, then the safety instance 18 initially passes on such a command to the robotic arm 8 as long as this is located within the permissible movement space, but while the robotic arm 8 is moving in obedience to the command it continuously calculates its position and terminates the command as soon as the boundary of the permissible movement space is reached.

In order to ensure that this boundary is not exceeded, the safety instance 18 can already reduce the speed of the robotic arm 8 before it reaches the boundary.

In the case of the third embodiment, it is generally simpler, using verbal commands, to specify the direction of a movement of the robotic arm 8 than its final position. Therefore, in this embodiment the safety instance 18 functions as described for the second embodiment.

As soon as the sensors 15 report a secure anchoring of the patient support 2 on the base 1, the safety instance 18 switches over from the park position to a permissible movement space above the patient support 2. At this point the robotic arm 8 is still located in the park position shown in FIG. 2 and thus outside of the new movement space. It can be arranged that in this case the safety instance 18 automatically steers the robotic arm 8 into a standby position in the new movement space, for example into the position shown in FIG. 1. However, it is also conceivable that a human operator controls such a movement via the execution instance 16. Since the robotic arm 8 is initially still located outside of the movement space, commands generated by the execution instance 16 cannot lead it out of the movement space; therefore, they are not suppressed by the safety instance 18.

If, at a later time, the patient support 2 is to be detached again from the base 1, and the handles 10 are extended for this purpose, according to one embodiment of the invention this leads to the bolts 14 disengaging from the recesses 13 and the sensors 15 reporting this to the safety instance 18, which reacts to this in that it once again specifies the park position shown in FIG. 2 as the movement space of the robotic arm 8 and simultaneously controls a movement of the robotic arm 8 into the park position. In this way, damage to the robotic arm 8 caused through carelessness when removing the patient support 2 or even a collision of the robotic arm 8 with a patient on the support 2 when moving the support 2 from the base 1 can be prevented.

According to an alternative embodiment, the safety instance 18 is connected with actuators 19 which, as indicated in FIG. 3 by a broken outline, are able to lock the bolts 14 in their recesses 13. Due to the coupling of the bolts 14 to the handles 10, this locking prevents the handles 10 from being extended, so that the patient support 2 cannot be removed as long as the locking is maintained. A user interface 20 of the safety instance 18, in the simplest case an individual button, makes it possible for a user to reset to the park position as movement space of the robotic arm 8, whereupon the safety instance 18 moves the robotic arm 8 into the park position and releases the locking, so that the patient support 2 can be removed.

FIG. 4 shows the robot system and the movement spaces of the robotic arm 8 according to a further developed embodiment of the invention in a diagrammatic side view. The movement space which the robotic arm 8 assumes in its park position, identified with 21, extends vertically downwards from the foot section 9 next to the column 4. The movement space 22 which the safety instance 18 selects after the patient support 2 is attached to the base 1 offers the robotic arm 8 greater freedom of movement. This is substantially limited in a downwards direction by the patient support 2 and in an upwards direction by the requirement not to collide with other objects, such as a camera 23 for example. Transversely to the plane of the drawing in FIG. 4, the movement space 22 can be limited by the requirement that the robotic arm 8 may not enter into the working areas of persons or, where present, of another robotic arm.

In the further developed embodiment shown in FIG. 4, the camera 23 and possibly a further camera 24 provide three-dimensional coverage of the patient support 2 and, if present, the body 25 of a patient. On the basis of the images supplied by the cameras 23, 24, the safety instance 18 is able to register the position of the body 25 in space and exclude this, possibly with the addition of a surrounding safety zone 26, from the movement space 22. In that the safety instance 18 then suppresses all commands addressed to the robotic arm 8 which would lead this out of the movement space 22, a contact of the robotic arm 8 with the body 25 is ruled out. While the robotic arm 8 is thus prevented from making direct contact with the patient, this is not the case for the—generally exchangeable—instrument 17 held by a robot head 31 of the robotic arm 8. It remains possible for this to make contact with the body 25 so that, for example, an incision can be made with a scalpel as end effector of an instrument 17 or an endoscope can be inserted into the body 25 as an instrument 17.

This rules out any potential injuries which could result from a direct contact of the robotic arm 8 with the body 25, for example when a surgeon is controlling the movement of the robotic arm 8 solely on the basis of images of the tip of the scalpel, or on the basis of images supplied by the endoscope, and fails to notice an impact of the robotic arm against the body 25.

Figure 5:
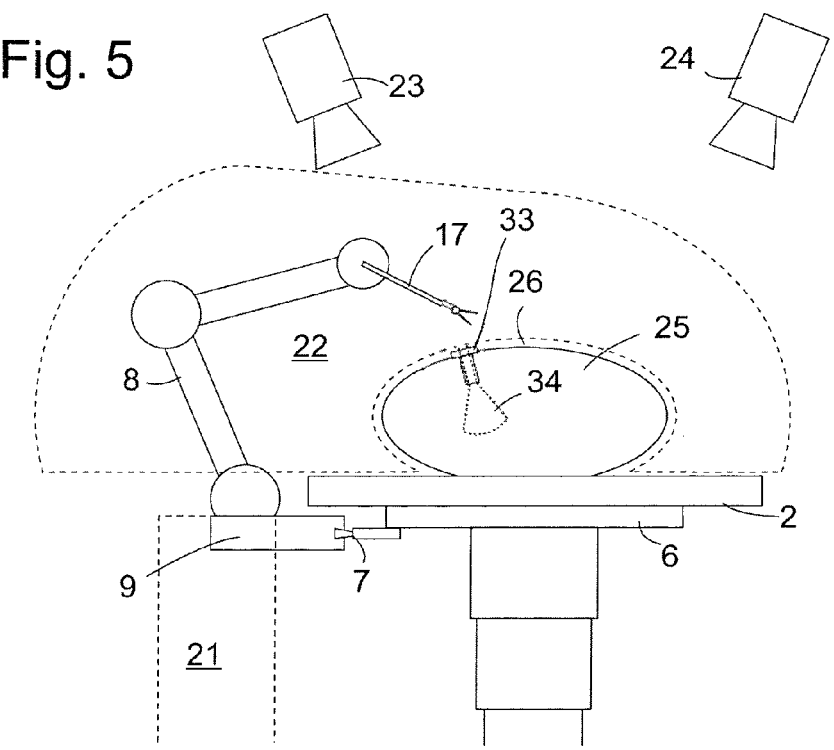
FIG. 5 shows a representation analogous to FIG. 4 according to a further development of the invention.

A further development of the concept described above, in particular with respect to minimally invasive operations, is illustrated in FIG. 5. Whereas in the case of FIG. 4 the range of the surgical instrument 17 guided by the robot head 31 of the robotic arm is substantially only limited by the requirement that the robot head 31 as part of robotic arm 8 may not leave the movement space 22, in the case shown in FIG. 5 the surgical instrument 17 is seen as being part of the robotic arm 8 and is thus subject to the limitation of freedom of movement to the movement space 22 described above. In order, nonetheless, to make possible a surgical operation with the aid of the instrument 17, in this case the movement space 22 overlaps with an area to be operated on in the body 25 of the patient.

In order to allow the instrument 17 to be introduced into the patient for the minimally invasive procedure, an access opening into the patient's body 25 has been made beforehand and is kept open by means of a port 33, for example a trocar sleeve, which is inserted into the patient. The movement space 22 comprises the passage of the trocar sleeve and the actual surgical field 34, which lies beyond the trocar sleeve in the body 25 of the patient. It is thus possible for the surgeon to thread the instrument 17 or at least its end effector into the port 33 and introduce it into the body 25 and to control the performance of the minimally-invasive procedure without having the instrument 17 breach the boundary of the movement space 22. An accidental injury to the body 25, both from outside and from inside, can thus be effectively prevented through an appropriately defined movement space 22, as shown for example in FIG. 5, since the surgical field 34 only extends into the body 25 as far as is necessary for the operation. Organs etc. which are to be protected are excluded from the surgical field 34.

Figure 6:
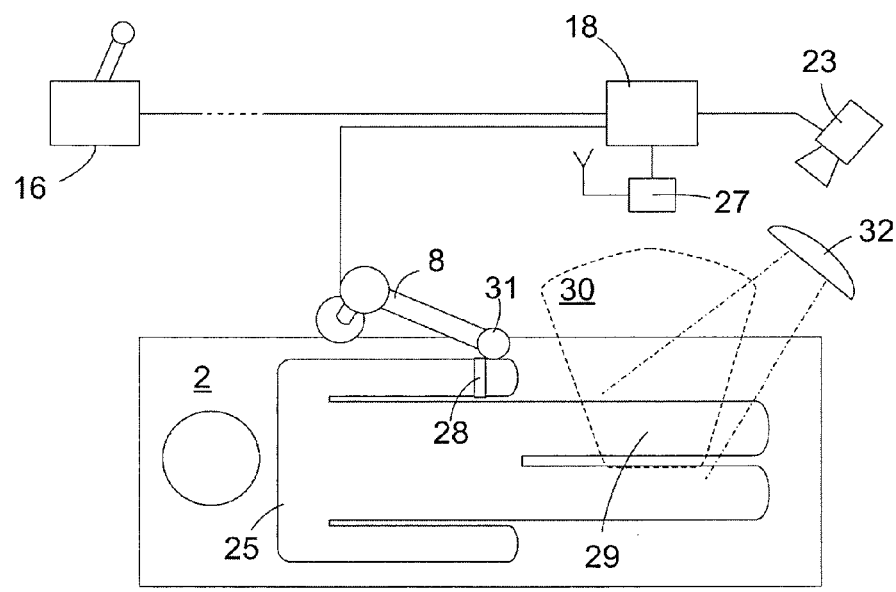
FIG. 6 shows a diagrammatic representation of a further developed embodiment of the robot system.

FIG. 6 illustrates a further development of the robot system according to the invention with reference to a diagrammatic top view of the patient support and of a patient lying thereon. The execution instance 16 is the same as described with reference to FIG. 3. The safety instance 18 can, as described with reference to FIG. 3, be connected with sensors for detecting the secure attachment of the patient support 2 to the base 1; however, this is not essential. The safety instance 18 is in this case connected with a data interface 27. This can be connected directly with a central IT system of the hospital in order to access data relating to the operation to be performed on the patient lying on the support 2. In the case illustrated here, the data interface 27 is an RFID radio interface which communicates with an RFID element 28 worn on the patient's body in order to access operation data stored thereon. It would also be conceivable only to receive the identity of the patient from the RFID element 28 and, based on this identity, to access the data relating to the operation from the central IT system. These data identify the body part which is to be operated on, in this case for example a left knee 29. With the aid of the camera 23 and suitable image processing software, the safety instance 18 is able to identify the relevant knee 29 on the body 25 of the patient and to define a movement space 30, matching the identified body part, within which the robotic arm 8 can move in order to perform the operation. This movement space 30 can lie completely outside of the body of the patient or, as described with reference to FIG. 5, also include a surgical field in the knee 29 into which a surgical tool of the robotic arm 8 is permitted to penetrate.

In the configuration shown in FIG. 6, the robotic arm 8 is mounted in proximity to the shoulder of the patient. It is neither located completely within the movement space 30 nor is its robot head 31 (or its surgical tool) able to reach each point of the movement space 30. The safety instance 18 recognizes this situation, for example on the basis of the images from the camera 23, and outputs a corresponding error message. The error message can be a text message on a monitor, but it is also conceivable that the safety instance 18 controls the orientation of a surgical lighting fixture 32 in order to alert the personnel to the need to correct the position of the robotic arm 8 through conspicuous illumination of the knee 29 or a point on the rail suitable for attachment of the robotic arm 8. Not only does this guarantee an appropriate positioning of the robotic arm 8, it also allows operation errors due to misidentification of the patient to be reliably ruled out.

REFERENCE NUMBERS 1. base element
2. patient support
3. base plate
4. column
5. segment
6. support plate
7. rail
8. robotic arm
9. foot section
10. handle
11. rib
12. groove
13. recess
14. bolt
15. sensor
16. execution instance
17. instrument
18. safety instance
19. actuator
20. user interface
21. movement space
22. movement space
23. camera
24. camera
25. body
26. safety zone
27. data interface
28. RFID element
29. knee
30. movement space
31. robot head
32. surgical lighting fixture
33. port
34. surgical field
35. base Modifications and substitutions by one of ordinary skill in the art are considered to be within the scope of the present invention, which is not to be limited except by the allowed claims and their legal equivalents.

The invention claimed is:

1. A surgical robot system comprising:
   a robotic arm (8) mounted on a base element (1);
   a controller, said controller comprising a first controller portion (16), configured for generating control commands for the robotic arm (8) on the basis of user inputs and a second controller portion (18), electrically coupled to said first controller portion (16) and to said robotic arm (8), and configured for receiving the control commands from the first controller portion (16) and for checking the control commands to determine whether execution of said control commands by the robotic arm (8) requires said robotic arm to leave a specified movement space (21, 22, 30) of the robotic arm (8), and responsive to said checking, for releasing a received control command for execution by the robotic arm (8) to the extent to which the received control command can be executed without the robotic arm leaving the specified movement space (21, 22, 30);

a patient support (2), detachably connectable to a support plate (6) mounted on the base element (1), wherein the second controller portion (18) is electrically coupled with at least one sensor (15) disposed in said support plate (6), and wherein said second controller portion (18) is configured for detecting whether the support plate (6) is connected with the patient support (2), and responsive to said detecting carried out by the second controller portion (18), said second controller portion (18) is configured for establishing different robotic arm movement spaces (21, 22) depending on whether or not the patient support (2) is detected as connected with the support plate (6) mounted on the base element (1), wherein if said second controller portion (18) detects that the support plate (6) is connected with the patient support (2), said second controller portion (18) establishes at least a first robotic arm movement space (22) allowing said robotic arm to move within said first robotic arm movement space (22), and if said second controller portion (18) detects that the support plate (6) is not connected with the patient support (2), said second controller portion (18) establishes a second robotic arm movement space (21) allowing said robotic arm to move only within said second robotic arm movement space (21).

2. The surgical robot system according to claim 1, characterised in that the at least one sensor (15) detects a position of a locking mechanism (14) in said support plate (6).

3. The surgical robot system according to claim 2, characterised in that said locking mechanism (14) in said support plate (6) is movable between a locked position in which it secures the patient support (2) to the support plate (6) mounted on the base element (1) and an unlocked position in which said locking mechanism (14) releases the patient support (2) from the support plate (6) mounted on the base element (1), and wherein said second controller portion (18) maintains said locking mechanism (14) in said locked position if said second controller portion (18) detects that the support plate (6) is connected with the patient support (2).

4. The surgical robot system according to claim 1, characterised in that the second controller portion (18) is coupled to a user interface (20), configured for allowing said second controller portion (18) to switch allowed movement of said robotic arm (8) between the movement spaces (21) and (22).

5. The surgical robot system according to claim 1, characterised in that a camera (23) is connected to the second controller portion (18).

6. The surgical robot system according to claim 5, characterised in that the camera (23) is arranged so as to scan a patient (25) on the patient support (2), and wherein the second controller portion (18) is configured to specify a movement space (22, 30) of the robotic arm (8) on the basis of a position of the patient (25) on said patient support (2).

7. The surgical robot system according to claim 1, characterised in that the second controller portion (18) further includes an interface (27) configured for receiving data relating to an operation to be performed on a patient (25) and is configured to specify the movement space (30) of the robotic arm (8) on the basis of said data relating to an operation to be performed on said patient (25).

8. The surgical robot system according to claim 7, characterised in that the second controller portion (18) is configured to check whether the specified movement space (30) is accessible for the robotic arm (8), and to generate an error message if at least a part of the movement space (30) is not accessible for the robotic arm (8).

9. The surgical robot system according to claim 1, characterised in that the robotic arm (8) can be mounted on the base element (1) in different positions.

10. The surgical robot system according to claim 9, characterised in that the second controller portion (18) is configured to detect the mounting position of the robotic arm (8) on the base element (1).

11. The surgical robot system according to claim 1, characterised in that the first robotic arm movement space (22) comprises a surgical field (34) in a body (25) of a patient.

12. The surgical robot system according to claim 11, characterised in that a part of the first robotic arm movement space (22) is located outside of the body (25) and wherein the surgical field (34) is located inside the body (25) and wherein said first robotic arm movement space (22) and said surgical field (34) are connected together via a port (33).

13. The surgical robot system according to claim 1, characterised in that the robotic arm (8) includes a surgical instrument (17) mounted thereon.

* * * * *